(12) United States Patent
Laudati

(10) Patent No.: US 10,918,190 B2
(45) Date of Patent: Feb. 16, 2021

(54) ROSE QUARTZ AND/OR JADE MULTI-ROLLER APPLICATOR AND CONTAINER APPARATUS

(71) Applicant: Kim A. Laudati, New York, NY (US)

(72) Inventor: Kim A. Laudati, New York, NY (US)

( * ) Notice: Subject to any disclaimer, the term of this patent is extended or adjusted under 35 U.S.C. 154(b) by 0 days.

(21) Appl. No.: 16/258,236

(22) Filed: Jan. 25, 2019

(65) Prior Publication Data

US 2020/0237073 A1    Jul. 30, 2020

(51) Int. Cl.
| | | |
|---|---|---|
| *B43K 23/08* | (2006.01) | |
| *A47L 13/12* | (2006.01) | |
| *A45D 34/04* | (2006.01) | |
| *A61M 35/00* | (2006.01) | |

(52) U.S. Cl.
CPC ......... *A45D 34/041* (2013.01); *A61M 35/003* (2013.01); *A45D 2200/051* (2013.01); *A45D 2200/10* (2013.01); *A61H 2201/105* (2013.01)

(58) Field of Classification Search
CPC .................................................... A45D 34/041
USPC ........................................... 401/209–217, 27
See application file for complete search history.

(56) References Cited

U.S. PATENT DOCUMENTS

| 2,103,261 A | * | 12/1937 | Hughes | ................. | A45D 27/10 |
| | | | | | 601/154 |
| 4,492,223 A | * | 1/1985 | Burke | .................... | A61H 15/02 |
| | | | | | 401/190 |
| 5,586,694 A | * | 12/1996 | Breidenbach | .......... | A45D 34/02 |
| | | | | | 222/183 |

FOREIGN PATENT DOCUMENTS

CN          109907961 A    *    6/2019

* cited by examiner

*Primary Examiner* — Jennifer C Chiang
(74) *Attorney, Agent, or Firm* — Michael L. Greenberg, Esq.; Greenberg & Lieberman, LLC

(57) ABSTRACT

A device configured to facilitate the application of a liquid solution to the surface of the skin of a user via a series of stone and/or crystal roller balls. The apparatus is equipped with several roller beads which are in contact with the solution. The solution is preferably housed within a container, and the roller beads are incorporated into a head and/or end of the container. The stone rollers ensure that the solution is applied evenly via multiple rolling points to deliver the solution to the skin from underneath the roller beads. Stone/crystal employed in the creation of the rollers is preferably rose quarts or jade, although other minerals may be used.

15 Claims, 5 Drawing Sheets

ROSE QUARTZ AND/OR JADE MULTI-ROLLER APPLICATOR AND CONTAINER APPARATUS

FIELD OF THE PRESENT INVENTION

The present invention relates to the field of cosmetics, and more specifically relates to a serum solution applicator embodied in a container equipped with a gemstone and/or stone roller applicator configured to be rolled along a face of a user to apply the serum solution.

BACKGROUND OF THE PRESENT INVENTION

A variety of facial rollers are currently present on the market. Some are tailored to solely use an elongated roller to remove puffiness from the face of a user, or to merely apply the therapeutic benefits of crystal therapy to the skin. Others facilitate the application of a liquid solution via a roller ball mechanism.

However, there are presently no known devices on the market configured to both apply a solution to the skin, as well as to employ a stone or crystal to the skin. Nearly every roller ball applicator container apparatus on the market employs a stainless steel ball or similar metallic ball to facilitate the application of the solution to the skin. If there were a container and roller application apparatus which employed stone or crystals to facilitate the application of a solution to the skin, the therapeutic benefits of materials such as jade and rose quartz could be applied to the user during the application of the solution.

In short, the market is presently lacking in roller applicators which employ non-metallic and non-plastic rollers for application of a liquid solution. Additionally, there are presently no roller applicators on the market configured to use multiple, or a series of rollers to facilitate a more substantial massaging sensation to the user during the application of the liquid solution.

Thus, there is a need for new roller applicator and container apparatus configured to ensure the adequate application of the liquid solution via a series of stone and/or crystal roller balls. Such an apparatus is preferably configured to hold the liquid solution, such as a beauty serum, within a container portion which maintains the unused solution in a sealed chamber which simultaneously ensures that the series of roller balls remains in contact with the solution. Such an apparatus preferably ensures that a user may enjoy the benefits of the serum, less waste of the serum, mess-free application of the serum, massage from the roller balls, as well as the therapeutic benefits of the crystal and/or stone employed in the creation of the roller balls.

SUMMARY OF THE PRESENT INVENTION

The present invention is an applicator and container apparatus equipped with a series of rolling balls disposed on a head of the apparatus. The series of rolling balls are preferably fashioned of a quality stone or crystal such as rose quartz or jade, which are known to be therapeutic to the skin and psyche of a user. When the apparatus is inverted (or a portion of the apparatus is squeezed), a solution contained within the container portion of the apparatus is disposed in contact with the series of rolling balls. When the rolling balls are rolled along the surface of the skin of a user, the solution contained within the container is released and applied to the skin of the user. Alternate embodiments of the container of the apparatus may be equipped with a squeezable component to facilitate dispensing of the serum from the applicator.

Unlike conventional roller-based applicators presently found on the market, the series of rolling balls of the present invention are composed of quality stone and/or crystal instead of conventional metals such as stainless steel. Additionally, unlike the standard single rolling ball found in conventional roller applicators found on the market, the present invention is equipped with multiple rolling balls, ranging from three to seven balls in a variety of patterns and orientations to facilitate ideal application of the solution of the container.

The roller balls of the present invention are preferably present in the form of rolling "beads" composed of rose quartz, and are available in multiple orientations. Similarly some embodiments may employ three, five, seven, or more rolling beads, which may be arranged in a variety of ways according to the preference of the user. Other embodiments of the present invention may employ two oblong gemstones configured to roll along the surface of the skin of a user in lieu of spherical beads. In short, the present invention preferably employs between two and seven beads or oblong gemstones to facilitate the rolling massage effect.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

The present invention will be better understood with reference to the appended drawing sheets, wherein.

DETAILED DESCRIPTION OF THE PREFERRED EMBODIMENT

Figure 1:
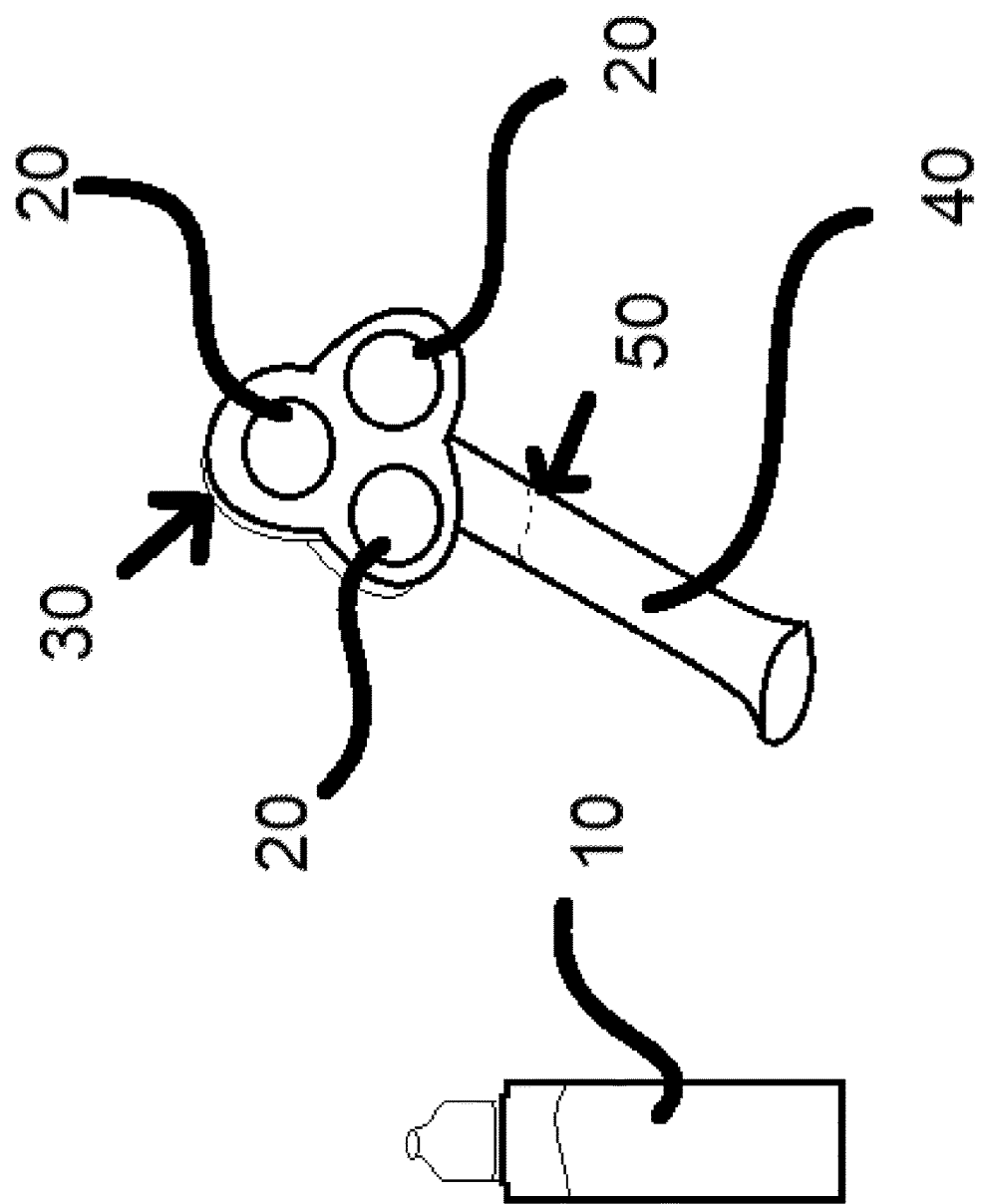
FIG. 1 depicts a view of the facial roller applicator and container apparatus of the present invention as seen from the top and side.
Figure 2:
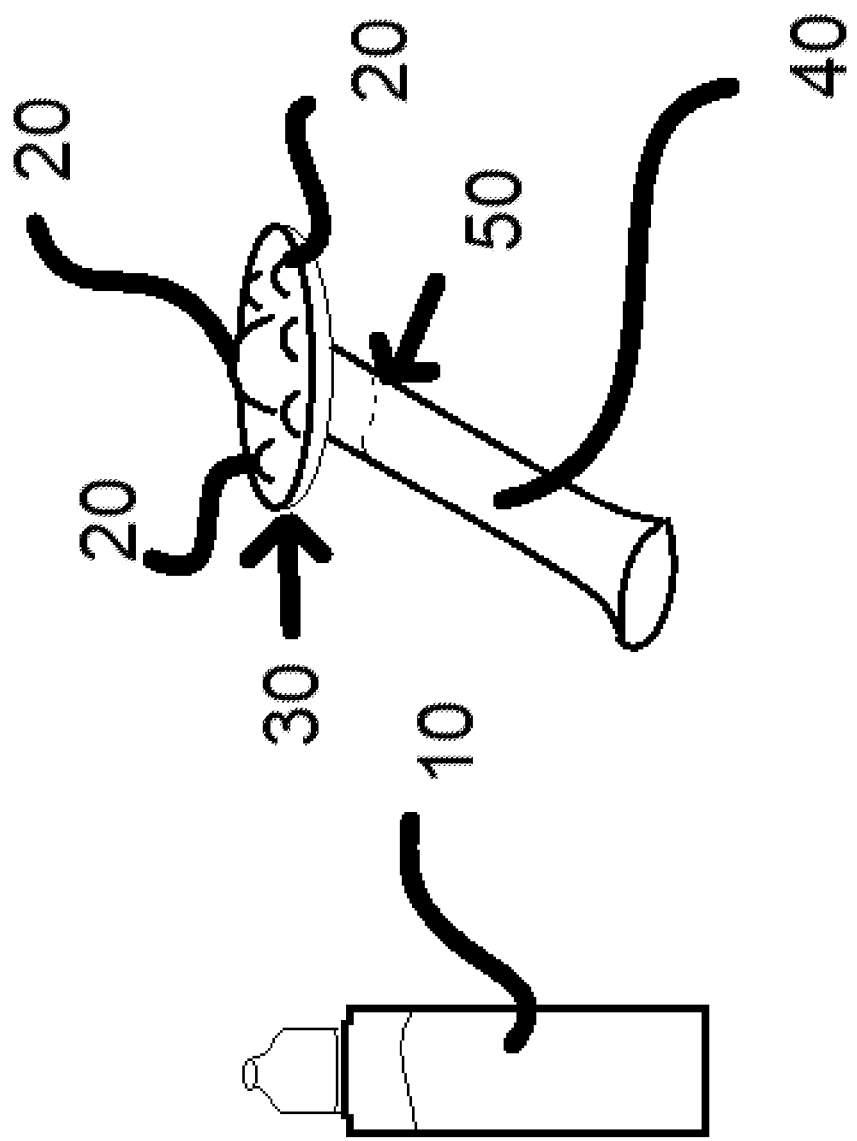
FIG. 2 displays a view of the facial roller applicator and container apparatus of the present invention equipped with the donut-styled head as seen from the top and side.

The present specification discloses one or more embodiments that incorporate the features of the invention. The disclosed embodiment(s) merely exemplify the invention. The scope of the invention is not limited to the disclosed embodiment(s). The invention is defined by the claims appended hereto.

References in the specification to "one embodiment," "an embodiment," "an example embodiment," etc., indicate that the embodiment described may include a particular feature, structure, or characteristic, but every embodiment may not necessarily include the particular feature, structure or characteristic. Moreover, such phrases are not necessarily referring to the same embodiment, Further, when a particular feature, structure, or characteristic is described in connection with an embodiment, it is submitted that it is within the knowledge of one skilled in the art to effect such feature, structure, or characteristic in connection with other embodiments whether or not explicitly described.

The present invention is a multi-roller applicator and container apparatus configured to facilitate the application of a liquid solution (10) to the surface of the skin of a user, such as to the skin of the face. Roller beads (20), embodied as small balls, are present on a head (30) of the apparatus. The head (30) is in communication with a container portion (40) equipped with a cavity (50). The liquid solution (10) is housed within the cavity (50) of the container portion (40), and is sealed via the head (30).

The head (30) of the apparatus is preferably removable from the container portion (40), and is affixed to the container portion (40) via threading or a snap-push seal. An o-ring may be present to ensure a firm seal is maintained between the head (30) of the applicator and the container portion (40).

When the apparatus of the present invention is inverted such that the roller beads (20) are at the bottom of the apparatus, the liquid solution (10) is brought into contact with a portion of the roller beads (20). When the roller beads (20) are rolled along the surface of the skin by a user, the liquid solution (10) is configured to be applied to the skin via the roller beads (20) as the roller beads (20) massage the skin's surface.

In one preferred embodiment of the present invention, three roller beads (20) are present atop the head (30) of the application of the present invention. In such an embodiment, the roller beads (20) are arranged in a triangular shape. In other preferred embodiments of the present invention, five roller beads (20) are present, and are preferably arranged such that one bead centrally disposed on the head, with the remaining four roller beads (20) arranged around the central bead. In other preferred embodiments, seven (or more) roller beads (20) may be present, similarly arranged with one or more central beads surrounded by the remaining roller beads (20).

Figure 3:
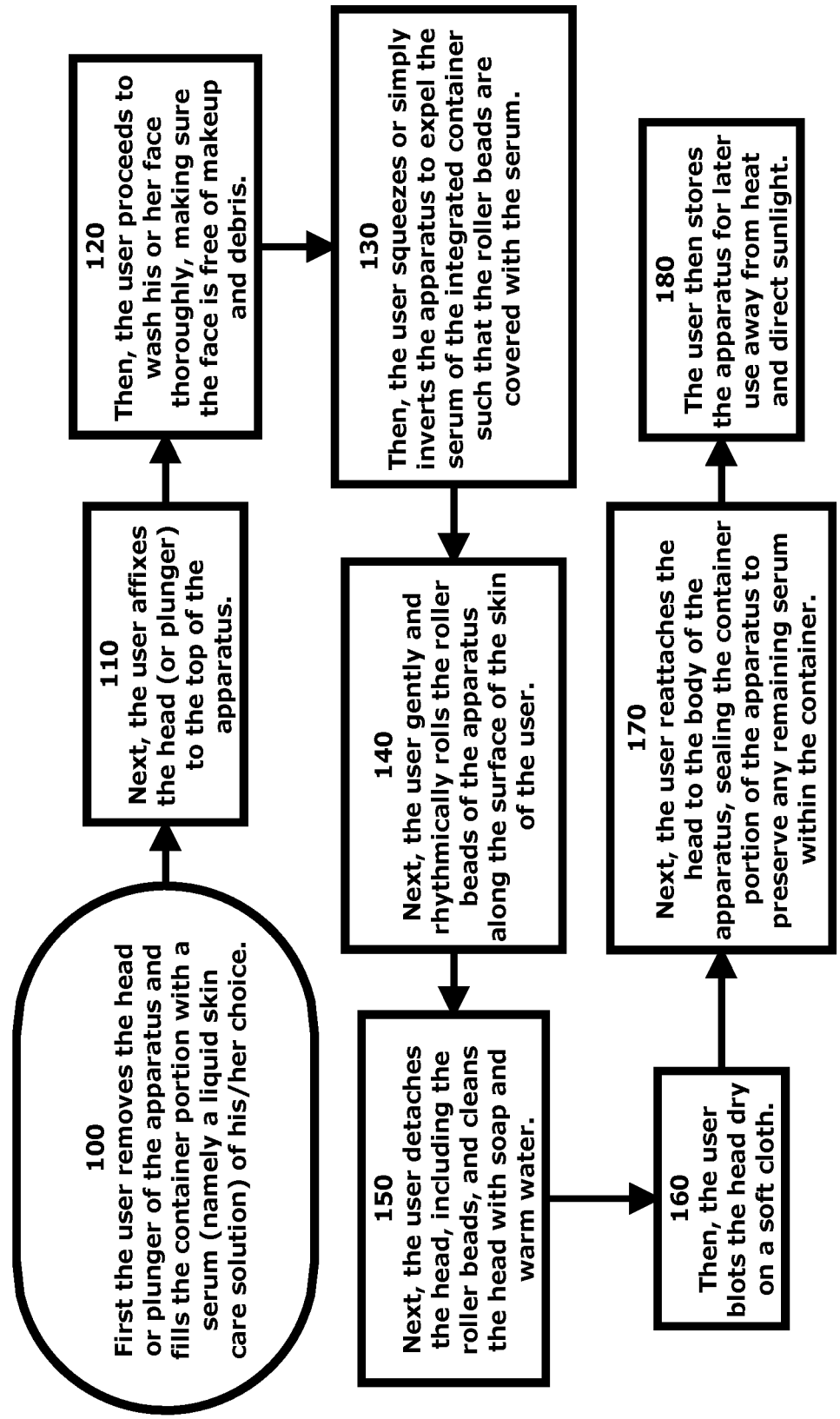
FIG. 3 exhibits a flow chart detailing the process of use of the apparatus of the present invention by an end user.

The process of use of the present invention, as depicted in FIG. 3, is preferably as follows:
1. First the user removes the head or plunger of the apparatus and fills the container portion with a serum (namely a liquid skin care solution) of his/her choice. (100)
2. Next, the user affixes the head (or plunger) to the top of the apparatus. (110)
3. Then, the user proceeds to wash his or her face thoroughly, making sure the face is free of makeup and debris. (120)
4. Then, the user squeezes or simply inverts the apparatus to expel the serum of the integrated container such that the roller beads are covered with the serum. (130)
5. Next, the user gently and rhythmically rolls the roller beads of the apparatus along the surface of the skin of the user. (140) The ideal progressive order of the application of the serum via the apparatus of the present invention is preferably as follows:
   a. Rolling the roller beads over a first side of one's neck.
   b. Rolling the roller beads over a second side of one's neck.
   c. Rolling the roller beads over a first side of one's lower face.
   d. Rolling the roller beads over a second side of one's lower face.
   e. Rolling the roller beads around one's mouth.
   f. Rolling the roller beads around a first eye, including a first half of one's forehead.
   g. Rolling the roller beads around a second eye, including a second half of one's forehead.
6. Next, the user detaches the head, including the roller beads, and cleans the head with soap and warm water. (150)
7. Then, the user blots the head dry on a soft cloth. (160)
8. Next, the user reattaches the head to the body of the apparatus, sealing the container portion of the apparatus to preserve any remaining serum within the container. (170)
9. The user then stores the apparatus for later use away from heat and direct sunlight. (180)

Preferred orientations of the roller beads (20) found on the head (30) of the present invention preferably include: a triangular orientation having three roller beads approximately equal in size arranged in triangle, a donut orientation having a large central roller bead circled by smaller roller beads, two large roller beads disposed at an angle with spacing between them to facilitate use of a single roller bead if desired, a single oblong roller bead in a horizontal orientation, dual oblong roller beads in a horizontal orientation, and other similar arrangements. Oblong roller beads are preferably 1 and ½ inches to two inches in length, however other sized roller beads may be instituted during manufacturing.

It should be understood that the cavity of the container portion (40) of the present invention is refillable by the user, and that any beauty serum may be placed within the cavity for use via the apparatus of the present invention. As such, each embodiment of the present invention is configured for reuse by the user. Additionally, some embodiments of the present invention may be purchased pre-filled with serum.

Figure 4:
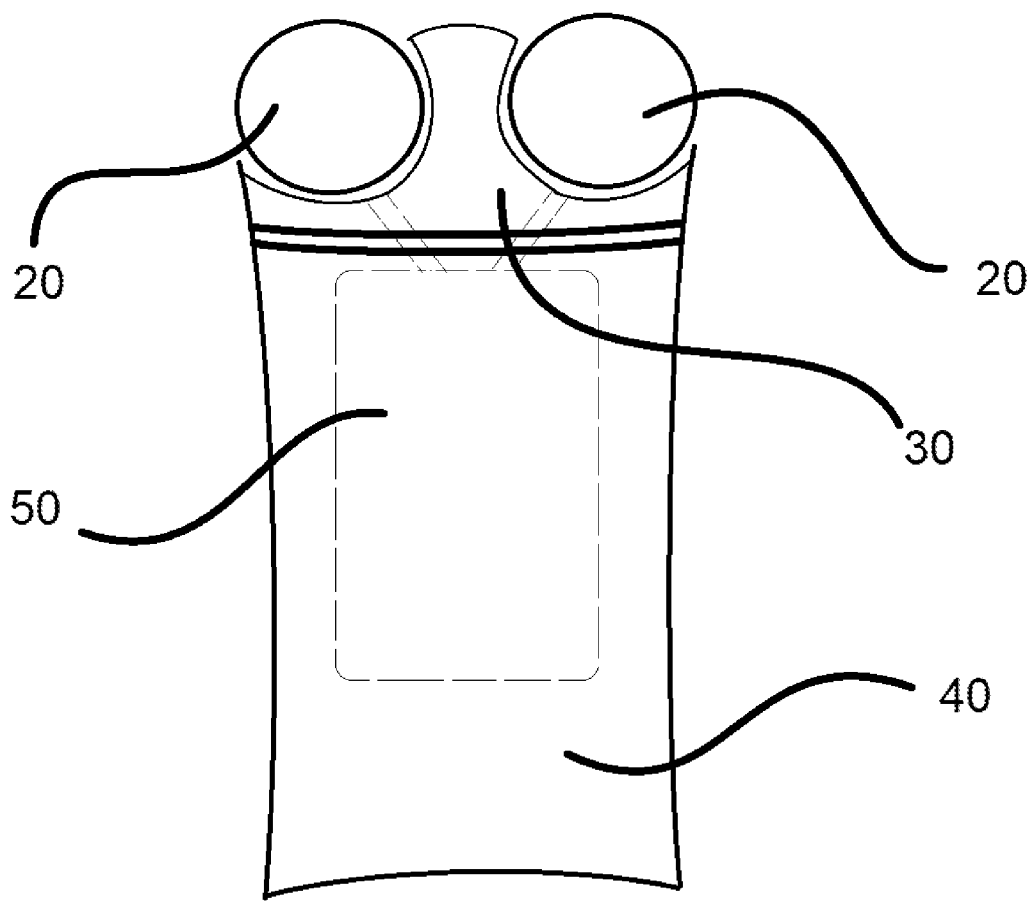
FIG. 4 depicts a first alternate embodiment of the present invention showing two elongated rollers as seen from the side.
Figure 5:
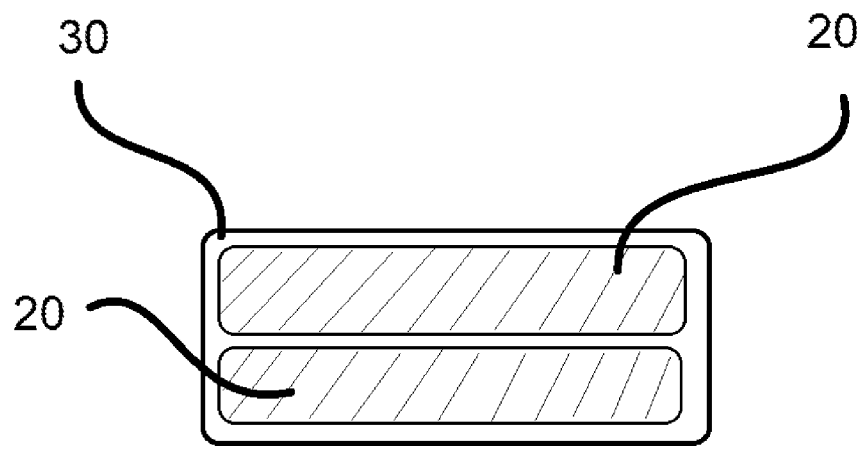
FIG. 5 exhibits the first alternate embodiment of the present invention showing two elongated rollers as seen from the top.
Figure 6:
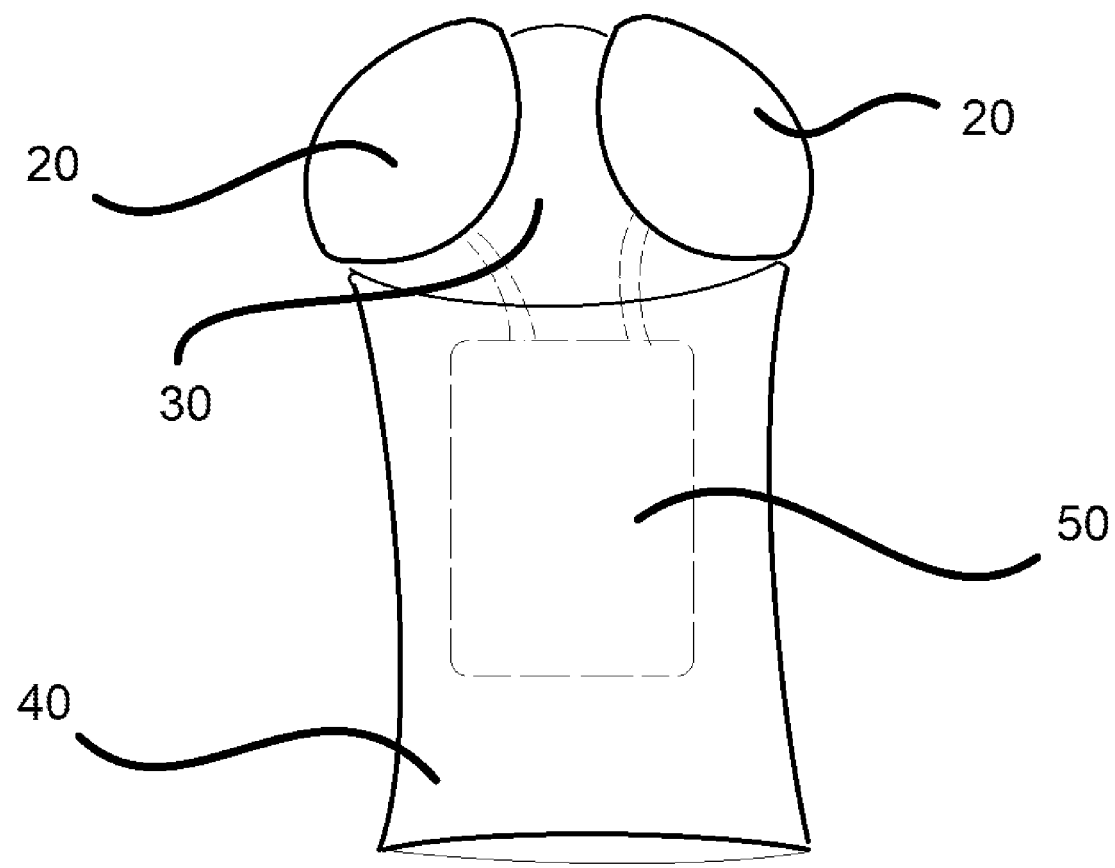
FIG. 6 shows a second alternate embodiment of the present invention having two centrally disposed roller balls which are slightly angled as seen from the side.
Figure 7:
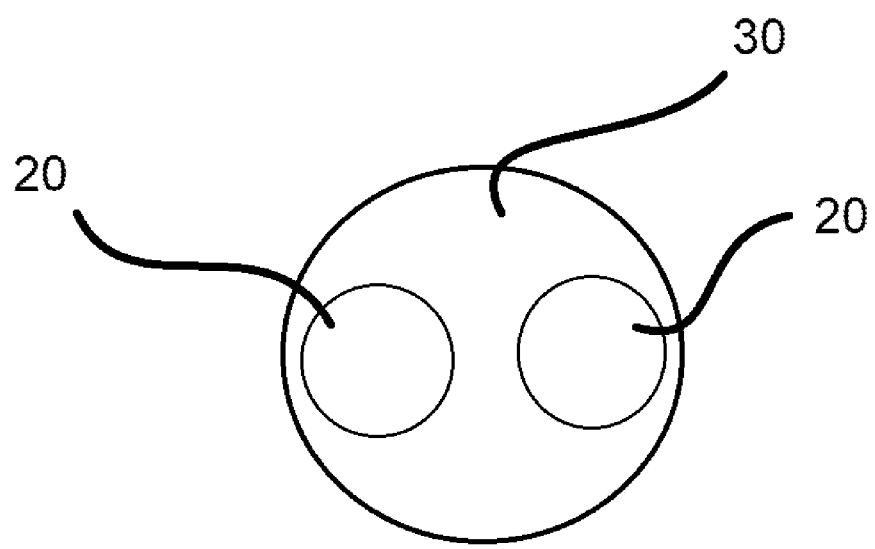
FIG. 7 shows the second alternate embodiment of the present invention as seen from the top.

Alternately, some embodiments of the present invention may be equipped (or bundled with) additional iterations of the head (30) to facilitate an interchangeable nature of the apparatus. As such, the user may opt to use oblong roller balls for some portions of the skin, such as the neck, and then switch out the head (30) equipped with oblong roller beads for a different iteration of the head (30) which has spherical roller beads (20). An embodiment with oblong, elongated rollers can be seen in FIG. 4 and FIG. 5. Other embodiments of the present invention may employ a head (30) which is fixed in position. In such instances, the user may then refill the container portion (40) with serum from a bottom of the apparatus, which is preferably equipped with a threaded lid.

It should be noted that the container portion (40) of the present invention is opaque, as the serum configured to be housed within the cavity of the container portion (40) is light-sensitive, and therefore should be kept in the dark to maintain efficacy and maximize the shelf life of the serum.

Some alternate embodiments of the present invention may vary in terms of scale. For example, a larger version of the present invention may be manufactured for more comfortable use on the body (rather than just the face), such as on the legs, arms, hands, and feet. In such embodiments, the roller beads (20), head (30), and container portion (40) are all larger in order to accommodate larger regions of the body, as well as to hold more serum.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

I claim:

1. An apparatus for use on the skin of a user comprising:
a container portion;
wherein said container portion is opaque;
a head, said head removably affixed to said container portion;
a cavity, said cavity disposed within said container portion;
roller beads, said roller beads centrally disposed on said head;
wherein said roller beads are made of one gemstone;
wherein said at least one gemstone is a gemstone selected from the following group: quartz and jade;
wherein said roller beads are in communication with said cavity;
wherein said cavity contains a liquid skin care serum; and
wherein said roller beads are a crystal.

2. The apparatus of claim 1, wherein said head is equipped with a means to permit passage of said serum to said at least one gemstone.

3. The apparatus of claim 2, wherein said container portion is equipped with a bottom; and
wherein said bottom is flat so as to permit vertical upright storage when not in use.

4. The apparatus of claim 2, wherein said bottom of said container portion is wider than a center of said container portion.

5. A therapeutic skin care apparatus for rejuvenating skin of a user comprising:
a body, said body equipped with a container portion disposed on a bottom portion of said body, and a head portion disposed on a top portion of said body;
wherein said head portion may be decoupled from said container portion;
at least two oblong rolling beads, said at least two oblong rolling beads amount to rollers;
wherein said rollers are composed solely of at least one gemstone;
wherein said bottom portion is flat;
a middle portion, said middle portion disposed between said top portion and said bottom portion;
wherein said bottom portion is wider than said middle portion;
wherein said container portion only contains a liquid skin care serum configured to facilitate skin rejuvenation when applied to the skin; and
wherein said rollers are configured to be rolled along the skin, in so doing, said liquid skin care serum is released onto said rollers, and applied to the skin.

6. The apparatus of claim 5, wherein said at least one gemstone is a crystal.

7. The apparatus of claim 5, wherein said liquid skin care serum is a serum fortified to nourish, remove puffiness, and de-wrinkle the skin.

8. The apparatus of claim 5, wherein said container portion is opaque.

9. The apparatus of claim 5, wherein all iterations of said at least one gemstone are a gemstone selected from the following group: rose quartz and jade.

10. The apparatus of claim 5, wherein all iterations of said at least one gemstone are jade.

11. The apparatus of claim 6, wherein said rollers are shorter in width than said container portion is in length.

12. The apparatus of claim 6, wherein said liquid skin care solution is a serum fortified to nourish, remove puffiness, and de-wrinkle the skin.

13. The apparatus of claim 6, wherein said container portion is opaque.

14. The apparatus of claim 7, wherein said container portion is opaque.

15. The apparatus of claim 5, wherein said rollers are unimpeded by any central protrusion, providing said rollers access to the skin without interference upon application.

* * * * *